United States Patent [19]

Fields

[11] 4,415,483
[45] Nov. 15, 1983

[54] CLASS OF FRIEDEL-CRAFTS CATALYSTS

[75] Inventor: Ellis K. Fields, River Forest, Ill.

[73] Assignee: Standard Oil Company (Indiana), Chicago, Ill.

[21] Appl. No.: 355,346

[22] Filed: Mar. 8, 1982

Related U.S. Application Data

[63] Continuation-in-part of Ser. No. 191,855, Sep. 29, 1980, abandoned.

[51] Int. Cl.³ .......................... B01J 29/00; B01J 21/02; B01J 27/02; B01J 27/20
[52] U.S. Cl. .................................. 502/255; 502/215; 502/220
[58] Field of Search ................ 252/439, 432, 443, 458

[56] References Cited

U.S. PATENT DOCUMENTS

| | | | |
|---|---|---|---|
| 1,868,532 | 7/1932 | Jaeger | 568/314 |
| 2,332,276 | 10/1943 | Stahly | 585/732 X |
| 2,415,817 | 2/1947 | Gohr et al. | 252/439 |
| 3,538,162 | 11/1970 | Dovell | 252/439 X |
| 3,996,256 | 12/1976 | Slough | 252/458 X |
| 4,073,866 | 2/1978 | Yamaki et al. | 252/443 X |

OTHER PUBLICATIONS

"Molybdenum Compounds", Killeffer et al., Interscience Pub., New York, London, 1952, p. 202.

*Primary Examiner*—William G. Wright
*Attorney, Agent, or Firm*—Gunar J. Blumberg; William T. McClain; William H. Magidson

[57] ABSTRACT

Molybdenum compounds, particularly molybdenum sulfide, molybdenum silicide, molybdenum selenide and molybdenum telluride are useful Friedel-Crafts catalysts for the aralkylation of aromatics to produce polybenzyls, the manufacture of aromatic ketones, aromtic sulfones and aromatic esters. The reaction products are useful as laminates, herbicides and bactericides.

1 Claim, No Drawings

CLASS OF FRIEDEL-CRAFTS CATALYSTS

This application is a continuation in part application of Ser. No. 191,855, filed Sept. 29, 1980, now abandoned.

FIELD OF THE INVENTION

The field of this invention relates to novel Friedel-Crafts Catalysts useful for the aralkylation of aromatics to produce polybenzyls, manufacture of aromatic ketones, aromatic sulfones and aromatic esters.

BACKGROUND

This invention relates to novel Friedel-Crafts Catalysts comprising molybdenum sulfide, molybdenum selenide and molybdenum silicide having a surface area of about 1.6 to 3.2 square meters per cubic centimeter, a mean diameter of about 3.3 to 5.4 microns and a particle size distribution of about 0.4 to 7.5 microns. These catalysts are adapted for use in the Friedel-Crafts reactions for the aralkylation of aromatics to produce polybenzyls, the manufacture of aromatic ketones, aromatic sulfones and aromatic esters.

It is an object of this invention to provide unique molybdenum containing compounds having carefully selected surface area, particle size distribution and mean diameter as catalysts for Friedel-Crafts reactions. Further objects and advantages will become apparent as the description of my invention proceeds.

The aralkylation of aromatic hydrocarbons to produce polybenzyls and the manufacture of ketones, sulfones and esters using various Friedel-Crafts Catalysts has been known to the prior art. For some of these reactions Grosse and Ipatieff in *J. Org. Chem.* 1, 559 (1936) showed the following order of reactivity of Friedel-Crafts type catalysts: $AlCl_3$ $ZrCl_4$ $TaCl_5$ $BF_3$ $CbCl_5$ $TiCl_4$. R. E. Bunk in Twelfth Catalysis Report, John Wiley and Sons, New York, p. 266 (1940) has disclosed a generalized table of reactivity, as follows: $AlBr_3$ $AlCl_3$ $FeCl_3$ $ZrCl_4$ $TaCl_5$ $BF_3$ $UCl_4$ $TiCl_3$ $WCl_6$ $CbCl_5$ $ZnCl_2$ $SnCl_4$ $TiCl_4$ $BeCl_2$ $SbCl_5$ $HgCl_2$ $CuCl_2$ $BiCl_3$ $AsF_3$.

The Friedel-Crafts Catalysts of the prior art have not been attractive in many instances due to the uncontrollable side reactions. The prior art Friedel-Crafts Catalysts also degrade under reaction conditions and during work-up, and are not recoverable. I have found that by employing molybdenum compounds such as molybdenum sulfide, molybdenum silicide, molybdenum selenide, and molybdenum telluride, having a surface area of about 1.6 to 3.3 square meters per cubic centimeter and having a particle size distribution of about 0.4 to 7.5 microns and a mean diameter of about 3.3 to 5.4 microns, the disadvantages of the prior art Friedel-Crafts Catalysts are overcome. This discovery is surprising and totally unexpected in regard to the prior art teachings, as the molybdenum compounds have been considered inert chemically. In fact, $MoS_2$ has been used widely as a lubricant because of its chemical unreactivity and related physical properties. Most molybdenum compounds are inert and only those disclosed herein and having the surface area, mean diameter and particle size distribution are useful as Friedel-Crafts Catalyst.

In comparison with the usual Friedel-Crafts Catalysts listed above, the molybdenum compounds of my invention are not consumed in the reactor and may be recovered from the reaction medium unchanged, therefore avoiding expensive and troublesome workup. My catalysts are also inexpensive, stable at elevated temperatures, cause no pollution and are environmentally inert.

My catalysts are particularly suitable for use in the aralkylation of aromatics to produce polybenzyls, for the manufacture of aromatic ketones from aroyl halides and aromatics, for the manufacture of aromatic sulfones from aryl sulfonyl halides and aromatics and for the manufacture of aromatic esters from aroyl halides and phenol and for the benzylation of polystyrene.

The aralkylation of aromatic hydrocarbons is carried out by contacting aromatic halides in the presence of the novel molybdenum-containing catalysts at a temperature and pressure effective for promoting the aralkylation under the catalytic influence of the aforementioned molybdenum compounds. The aralkylation usually is conducted at a temperature of about 60° to 250° C. and the catalyst concentration is in the range of about 0.01 to about 15 percent by weight of reactants. The novel aralkylation process is suitable for the production of polybenzyls from benzyl halides and halogenated xylenes. In like manner, using applicant's novel catalyst ketones are produced from aroyl halides and aromatics and sulfones are produced from aryl sulfonyl halides and aromatics. Similarly, esters are formed from aroyl halides and phenols. In all these reactions, the reaction temperature is kept in the range of about 60° to 250° C. and if more than one reactant is present, the mole ratio of the reactants is about 1:1 to 3:1. The molybdenum catalyst is usually employed at a concentration of about 0.01 to 15 percent by weight of the reactant. In some instances the reaction is conducted in the presence of inert hydrocarbon solvents such as benzene or xylene. The polybenzyls produced by the novel aralkylation process are useful as laminants and glass reinforced laminants. The ketones, particularly methylated benzophenones are useful as herbicides. The methylated diphenylsulfones and the related aroyl sulfones are used as stabilizers for polyesters.

The following examples illustrate the preferred embodiment of this invention. It will be understood that these examples are for illustrative purposes only and do not purport to be wholly definitive with respect to conditions or scope of the invention.

EXAMPLE 1

A mixture of 34.5 ml (0.3 mole) of benzyl chloride and 4.8 g (30 millimoles) of molybdenum disulfide, $MoS_2$ having a surface area of 1.6 to 1.8 square meters per cubic centimeter, a mean diameter of 4.9 to 5.4 microns, and a particle size distribution of 0.1 to 7.5 microns, was heated at 75°–80° C. for 96 hours. Hydrogen chloride evolved steadily, diminishing in intensity after 48 hours and ceasing by 96 hours. Benzene, 100 ml, was added and the mixture was stirred and refluxed 2 hours, then filtered. The weight of recovered molybdenum disulfide was 4.8 g.

The benzene solution of polybenzyl was viscous and highly fluorescent. It had adhesive properties. It was evaporated to recover 27 g (100 mole percent yield) of hard, solid polybenzyl.

Analysis: Calcd. for $(C_7H_6)_n$: C, 93.3 percent; H, 6.7 percent; Fd.: C, 92.9 percent; H, 6.7 percent; Cl, 0.1 percent.

Intrinsic viscosity, 2 percent in toluene, 0.05.

EXAMPLE 2

A mixture of 3.02 g (20 millimoles) of molybdenum disilicide, MoSi$_2$, having a surface area of 1.5 to 2 square meters per cubic centimeter, a mean diameter of 4.1 to 4.8 microns, and a particle size distribution of 0.6 to 7.5 microns and 22.3 ml (0.2 mole) of benzyl chloride was stirred and heated. At 80° C. hydrogen chloride evolved in copious amount and the temperature of the mixture rose to 106° C. in 5 minutes. The mixture became viscous, then solidified. It was kept at 83° C. for 16 hours, dissolved in 100 ml of hot benzene, filtered, and evaporated to give 18.0 (100 mole percent yield) of solid polybenzyl that analyzed 92.9 percent C, 6.3 percent H, Cl 0.1 percent. The intrinsic viscosity (IV), 2 percent in toluene, was 0.07. The recovered MoSi$_2$ weighed 3.02 g.

EXAMPLE 3

A solution of 28.2 ml (0.2 mole) of vinylbenzyl chloride (Dow Experimental monomer XD-1915, 60 percent m-and 40 percent p-vinylbenzyl chloride containing 50 ppm of tert-butylcatechol and 1000 ppm of nitromethane) in 100 ml of benzene was refluxed 24 hours to give a viscous solution of polymer. A mixture of 25.6 ml of solution, containing 40 millimoles calculated as monomeric vinylbenzyl chloride, and 0.035 g (0.1 millimole) of molybdenum ditelluride, MoTe$_2$, having a particle size distribution of 0.6 to 7.5 microns, a mean diameter of about 3.6 to 3.9 microns and a surface area of about 2.9 to 3.3 square meters per cubic centimeter, was stirred and heated to remove benzene, then at 120° C. for 1 hour. HCl evolved. Commercial xylene, 50 ml, was added; the mixture was stirred and refluxed for 2 hours, at which time no more HCl evolved. The xylene solution was poured into 300 ml of methanol to precipitate 4.7 g of white polymer that analyzed C, 89.8 percent; H, 8.4 percent; Cl, 0.6 percent. IV, 2 percent in o-dichlorobenzene, 0.29.

EXAMPLE 4

A mixture of 28.56 ml (0.2 mole) of benzyl chloroformate,

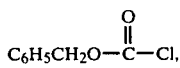

and 1 g (3 mole percent) of MoS$_2$ having a surface area of 1.6 to 1.8 square meters per cubic centimeter, a mean diameter of 4.9 to 5.4 microns and a particle size distribution of 0.1 to 7.5 microns, was stirred and warmed. At 52° C. gas evolved at an increasing rate and the temperature rose to 125° C. When the spontaneous heat had subsided, the mixture was kept at 90° C. for 1 hour, treated with 100 ml of toluene, filtered from MoS$_2$ (1 g recovered) and evaporated to give 22 g of light-brown, clear, hard polymer that analyzed C, 89.9 percent; H, 6.3 percent; Cl, 0.2 percent; IV, 2 percent in o-dichlorobenzene, 0.06.

EXAMPLE 5

A mixture of 23 ml (0.2 mole) of benzyl chloride and 11.5 ml (0.1 mole) of freshly distilled styrene was heated at 60° C. for 15 hours. To the viscous solution was added 0.351 g (1 millimole) of MoTe$_2$ having a particle size distribution of 0.6 to 7.5 microns, a mean diameter of about 3.6 to 3.9 microns and a surface area of about 2.9 to 3.3 square meters per cubic centimeter. The stirred mixture was heated at 140° C. for 3 hours, HCl evolving in great quantities; 50 ml of commercial xylene were added, stirring and refluxing continued for 4 hours. The hot solution was filtered into 300 ml of methanol, precipitating 13 g of brown solid polymer that analyzed 92.9 percent C; 6.8 percent H; and 0.22 percent Cl.

EXAMPLE 6

A mixture of 23 ml of (0.2 mole) of benzyl chloride and 23 ml (0.2 mole) of freshly-distilled styrene was treated as in Example 5 to give 20.5 g of rubbery copolymer that analyzed 92.3 percent C, 7.6 percent H, and 0.1 percent Cl.

EXAMPLE 7

A mixture of 23 ml (0.2 mole) of benzyl chloride and 34.5 ml (0.3 mole) of styrene was treated as in Example 5 to give 32.3 of rubbery copolymer that analyzed 92.8 percent C, 7.2 percent H, and 0.04 percent Cl.

EXAMPLE 8

A mixture of 16 ml (0.139 mole) of styrene and 7.05 ml (0.05 mole) of vinylbenzyl chloride was treated as in Example 5 to give 7.7 g of white, solid polymer that analyzed 83.6 percent C, 6.8 percent H, and 8.2 percent Cl.

| IV. 2% in o-dichlorobenzene | Product of Example |
|---|---|
| 0.13 | 5 |
| 0.20 | 6 |
| 0.30 | 7 |
| 0.73 | 8 |

EXAMPLE 9

A mixture of 10.4 g of crystal polystyrene, IR3CO 8A-PED-648, 0.1 mole calculated as styrene, 11.5 ml (0.1 mole) of benzyl chloride, 30 ml of 1,2,4-trichlorobenzene, and 0.2 g of MoTe$_2$ was stirred at 75° C. for 2.5 hours, HCl evolving rapidly. Benzene (100 ml) was added, the solution filtered from MoTe$_2$ having a surface area of 1.5 to 2 square meters per cubic centimeter, a mean diameter of 4.1 to 4.8 microns, and a particle size distribution of 0.6 to 7.5 microns, and a little gelled polymer, and poured into 200 ml of isopropanol. The precipitated polymer was redissolved in benzene and reprecipitated by isopropanol to give 16.8 g of white benzylated polystyrene that analyzed 92.8 percent C and 6.6 percent H.
IV 2 percent in toluene
Original polystyrene, 0.7
Benzylated polystyrene, 1.09

EXAMPLE 10

A mixture of 9.4 g (0.1 mole) of phenol, 11.51 ml (0.1 mole) of benzyl chloride, and 0.176 g (0.5 millimole) of MoTe$_2$ having a surface area of 1.5 to 2 square meters per cubic centimeter, a mean diameter of 4.1 to 4.8 microns and a particle size distribution of 0.6 to 7.5 microns, was kept at 55°–65° C. for 24 hours, at which time HCl evolution had stopped. The mixture was diluted with 100 ml of benzene, filtered from MoTe$_2$, and evaporated to give 18.4 g of cream-colored solid, all soluble in aqueous base, that contained 4- and 2-benzylphenols in the ratio of 1.4:1.

EXAMPLE 11

A mixture of 9.4 g (0.1 mole) of phenol, 11.6 g (0.1 mole) of benzoyl chloride and 0.176 g (0.5 millimole) of $MoTe_2$ having a surface area of 1.5 to 2 square meters per cubic centimeter, a mean diameter of 4.1 to 4.8 microns and a particle size distribution of 0.6 to 7.5 microns, was warmed at 30° C. There was a vigorous evolution of HCl. After 1 hour the entire mixture had solidified. It was heated at 60° C. for 2 hours, the solid was broken up, washed with water, dissolved in acetone, filtered from $MoTe_2$, and evaporated to give 17.6 g (89 mole percent) of white crystalline phenyl benzoate, Mp and mixed mp 70° C.

EXAMPLE 12

A mixture of 15.46 g (0.1 mole) of m-toluoyl chloride, 24.6 ml (0.2 mole) of p-xylene, and 2 g of $MoS_2$ having a surface area of 1.6 to 1.8 square meters per cubic centimeter, a mean diameter of 4.9 to 5.4 microns and a particle size distribution of 0.1 to 7.5 microns, was stirred and refluxed. After 24 hours no more HCl evolved. The mixture was diluted with 100 ml of benzene, filtered from 2 g of $MoS_2$ and distilled to obtain 12.5 g boiling at 245°-250° C./200 of 2,4,3-trimethylbenzophenone, 82.6 mole percent yield.

EXAMPLE 13

A mixture of 24.6 ml (0.2 mole) of p-xylene, 19.0 g (0.1 mole) of p-toluene sulfonylchloride, and 0.2 g of $MoTe_2$ having a particle size distribution of 0.6 to 7.5 microns, a mean diameter of about 3.6 to 3.9 microns, and a surface area of about 2.9 to 3.3 square meters per cubic centimeter, was stirred and heated at 146° C. After 24 hours no more HCl evolved. The cooled mixture was diluted with 100 ml of benzene, filtered from $MoTe_2$, and evaporated to obtain 26.6 g (100 mole percent) of 2,5,4'-trimethyl diphenyl sulfone, mp 108°-109° C. from isopropanol. H. Drews, S. Meyerson, and E. K. Fields, *J. Am. Chem. Soc.*, 83, 3871 (1969) gave the mp as 108°-110° C.

EXAMPLE 14

A mixture of 5.01 g (20 millimoles) of molybdenum diselenide, $MoSe_2$, having particle size distribution of about 0.6 to 6 microns, a mean diameter of about 3.3 to 3.6 microns and a surface area of about 2.2 to 2.5 square meters per cubic centimeter, and 44.6 ml. (0.4 mole) of benzylchloride was stirred and heated to 80° C. Hydrogen chloride evolved copiously, and the temperature of the mixture rose to 114° C. over 7 minutes. The mixture became more and more viscous, and solidified after 15 minutes. It was kept at 85° C. for 16 hours, dissolved in 200 ml. of hot benzene, filtered and evaporated, yielding 36 g (100 mole percent yield) of solid polybenzyl that analyzed C, 93.0 percent; H, 6.5 percent; Cl, 0.1 percent. The intrinsic viscosity, 2 percent in toluene, was 0.09. The recovered $MoSe_2$ weighed 5 g.

I claim:

1. A catalyst for the aralkylation of aromatics to produce polybenzyls, manufacture of aromatic ketones, aromatic sulfones and aromatic esters wherein the catalyst is molybdenum silicide, having a particle size distribution of about 0.6 to 7.5 microns and a mean diameter of about 4.1 to 4.8 microns and a surface area of about 1.5 to 2 square meters per cubic centimeter.

* * * * *